US011445963B1

(12) United States Patent
Belicev et al.

(10) Patent No.: US 11,445,963 B1
(45) Date of Patent: Sep. 20, 2022

(54) METHOD AND APPARATUS FOR RECONSTRUCTING ELECTROCARDIOGRAM (ECG) DATA

(71) Applicant: HeartBeam, Inc., Santa Clara, CA (US)

(72) Inventors: Petra Belicev, Santa Clara, CA (US); Bosko Bojovic, Belgrade (RS); Ljupco Hadzievski, Belgrade (RS); Branislav Vajdic, Los Gatos, CA (US); Vladimir Atanasoski, Belgrade (RS); Goran Gligoric, Belgrade (RS); Marjan Miletic, Belgrade (RS)

(73) Assignee: HeartBeam, Inc., Santa Clara, CA (US)

( * ) Notice: Subject to any disclaimer, the term of this patent is extended or adjusted under 35 U.S.C. 154(b) by 0 days.

(21) Appl. No.: 17/494,806

(22) Filed: Oct. 5, 2021

(51) Int. Cl.
| | |
|---|---|
| *A61B 5/327* | (2021.01) |
| *A61B 5/332* | (2021.01) |
| *A61B 5/28* | (2021.01) |
| *A61B 5/00* | (2006.01) |
| *A61B 5/339* | (2021.01) |

(52) U.S. Cl.
CPC .............. *A61B 5/327* (2021.01); *A61B 5/28* (2021.01); *A61B 5/332* (2021.01); *A61B 5/339* (2021.01); *A61B 5/7253* (2013.01)

(58) Field of Classification Search
None
See application file for complete search history.

(56) References Cited

U.S. PATENT DOCUMENTS

| | | | |
|---|---|---|---|
| 4,216,780 | A | 8/1980 | Rubel |
| 4,850,370 | A | 7/1989 | Dower |
| 5,630,664 | A | 5/1997 | Farrelly |
| 5,724,580 | A | 3/1998 | Levin et al. |
| 6,047,203 | A | 4/2000 | Sackner et al. |
| 6,052,615 | A | 4/2000 | Feild et al. |

(Continued)

FOREIGN PATENT DOCUMENTS

| | | |
|---|---|---|
| CN | 1668242 A | 9/2005 |
| CN | 1870937 A | 11/2006 |

(Continued)

OTHER PUBLICATIONS

Dower et al.; A clinical comparison of three vcg lead systems using resistance-combining networks; American Heart Journal; 55(4); pp. 523-534; Apr. 1958.

(Continued)

*Primary Examiner* — Kennedy Schaetzle
(74) *Attorney, Agent, or Firm* — Shay Glenn LLP

(57) ABSTRACT

Systems and apparatus for synthesizing (generating) 12-lead ECG dataset from 3-lead ECG data. In particular, one or more transformation parameters may be determined that may be applied to 3-lead ECG dataset to generate 12-lead ECG data with particular speed and accuracy. The transformation parameters, which may include a plurality of matrices, may be determined from a synchronized patient's 12-lead ECG dataset and 3-lead ECG data. The 12-lead ECG dataset may be collected at a different time than the 3-lead ECG data. In some embodiments, the 12-lead ECG dataset and/or the 3-lead ECG dataset may be resampled prior to determining the transformation parameters.

21 Claims, 10 Drawing Sheets

(56) References Cited

U.S. PATENT DOCUMENTS

| | | |
|---|---|---|
| 6,363,274 B1 | 3/2002 | Scalisi et al. |
| 6,607,480 B1 | 8/2003 | Bousseljot et al. |
| 6,625,483 B2 | 9/2003 | Hoium et al. |
| 7,266,408 B2 | 9/2007 | Bojovic et al. |
| 7,477,935 B2 | 1/2009 | Palreddy et al. |
| 7,647,093 B2 | 1/2010 | Bojovic et al. |
| 8,369,936 B2 | 2/2013 | Farringdon et al. |
| 8,615,290 B2 | 12/2013 | Lin et al. |
| 8,700,137 B2 | 4/2014 | Albert |
| 8,818,482 B2 | 8/2014 | Phillips et al. |
| 9,364,158 B2 | 6/2016 | Banet et al. |
| 10,117,592 B2 | 11/2018 | Bojovic et al. |
| 10,433,744 B2 | 10/2019 | Bojovic et al. |
| 11,071,490 B1 | 7/2021 | Vajdic et al. |
| 2002/0045836 A1 | 4/2002 | Alkawwas |
| 2003/0032871 A1 | 2/2003 | Selker et al. |
| 2003/0083586 A1 | 5/2003 | Ferek-Petric |
| 2003/0216655 A1* | 11/2003 | Schreck ............... A61B 5/327 600/509 |
| 2004/0087864 A1 | 5/2004 | Grouse |
| 2005/0027203 A1 | 2/2005 | Umeda et al. |
| 2005/0215918 A1 | 9/2005 | Frantz et al. |
| 2005/0234354 A1 | 10/2005 | Rowlandson et al. |
| 2006/0009698 A1 | 1/2006 | Banet et al. |
| 2006/0224072 A1 | 10/2006 | Shennib |
| 2007/0021677 A1 | 1/2007 | Markel |
| 2008/0027330 A1 | 1/2008 | Naghavi et al. |
| 2008/0113650 A1 | 5/2008 | Engstrom |
| 2008/0161715 A1 | 7/2008 | Stivoric et al. |
| 2009/0112105 A1 | 4/2009 | Clayman |
| 2009/0281421 A1 | 11/2009 | Culp et al. |
| 2009/0281440 A1 | 11/2009 | Farazi et al. |
| 2009/0299206 A1 | 12/2009 | Wang et al. |
| 2010/0076331 A1 | 3/2010 | Chan et al. |
| 2010/0130845 A1* | 5/2010 | Clayman ............... A61B 5/68 600/382 |
| 2010/0174204 A1 | 7/2010 | Danteny |
| 2010/0240980 A1 | 9/2010 | Zhu et al. |
| 2011/0015496 A1 | 1/2011 | Sherman et al. |
| 2011/0105928 A1 | 5/2011 | Bojovic et al. |
| 2011/0301435 A1 | 12/2011 | Albert et al. |
| 2011/0306859 A1 | 12/2011 | Saldivar et al. |
| 2012/0022385 A1 | 1/2012 | Shimuta |
| 2012/0059271 A1 | 3/2012 | Amitai et al. |
| 2012/0116176 A1 | 5/2012 | Moravec et al. |
| 2012/0116240 A1 | 5/2012 | Chou |
| 2012/0136266 A1 | 5/2012 | Grady |
| 2012/0184858 A1 | 7/2012 | Harlev et al. |
| 2012/0283586 A1 | 11/2012 | Song et al. |
| 2013/0125906 A1 | 5/2013 | Hon |
| 2013/0172723 A1 | 7/2013 | Baxi et al. |
| 2014/0114166 A1 | 4/2014 | Baxi |
| 2014/0155723 A1 | 6/2014 | Levin et al. |
| 2014/0163349 A1 | 6/2014 | Amitai et al. |
| 2014/0257122 A1 | 9/2014 | Ong et al. |
| 2015/0057512 A1 | 2/2015 | Kapoor |
| 2016/0015286 A1* | 1/2016 | Gitlin ............... A61N 1/36514 600/512 |
| 2016/0022162 A1 | 1/2016 | Ong et al. |
| 2016/0135706 A1 | 5/2016 | Sullivan et al. |
| 2016/0188823 A1 | 6/2016 | Rowlandson et al. |
| 2016/0287172 A1 | 10/2016 | Morris et al. |
| 2017/0127966 A1 | 5/2017 | Wu et al. |
| 2018/0004904 A1 | 1/2018 | Phillips |
| 2018/0064356 A1 | 3/2018 | Mendenhall et al. |
| 2019/0069789 A1 | 3/2019 | Bojove et al. |
| 2019/0117100 A1 | 4/2019 | Rollie et al. |
| 2019/0336020 A1 | 11/2019 | Kranz |
| 2020/0113454 A1 | 4/2020 | Wu et al. |
| 2020/0315480 A1 | 10/2020 | Hwang |
| 2020/0375493 A1 | 12/2020 | Kranz |
| 2021/0113136 A1 | 4/2021 | Bojovic et al. |
| 2021/0169392 A1 | 6/2021 | Albert et al. |
| 2022/0061759 A1 | 3/2022 | Galeev et al. |

FOREIGN PATENT DOCUMENTS

| | | |
|---|---|---|
| CN | 101524272 A | 9/2009 |
| CN | 202854760 U | 4/2013 |
| CN | 203000927 U | 6/2013 |
| EP | 0944353 B1 | 11/2002 |
| EP | 1659936 A1 | 3/2005 |
| WO | WO01/70105 A2 | 9/2001 |
| WO | WO2017/208040 A2 | 12/2017 |
| WO | WO2020/0232040 A1 | 11/2020 |

OTHER PUBLICATIONS

Goff et al.; 2013 ACC/AHA guideline on the assessment of cardiovascular risk: a report of the American College of Cardiology/ American Heart Association Task Force on Practice Guidelines; Journal of the American College of Cardiology; 63(25 Part B); pp. 2935-2959; Jul. 1, 2014.

Kligfield et al.; Recommendations for the standardization and interpretation of the electrocardiogram: Part I: The Electrocardiogram and its Technology A Scientific Statement From the American Heart Association Electrocardiography and Arrhythmias Committee, Council on Clinical Cardiology; the American College of Cardiology Foundation; and the Heart Rhytnm Society Endorsed by the International Society for Computerized Electrocardiology; 49(10); pp. 1109-1127; Mar. 13, 2007.

Marma et al.; Systematic examination of the updated Framingham heart study general cardiovascular risk profile; Circulation; 120(5): pp. 384; Aug. 1, 2009.

MED-TECH Innovation; The ECG device the of a credit card; Aug. 23, 2017; retrieved from the internet (https://www.med-technews.com/news/the-ecg-device-the-size-of-a-credit-card/) on Jan. 26, 2021.

Perk et al.; European Guidelines on cardiovascular disease prevention in clinical practice (version 2012) The Fifth Joint Task Force of the European Society of Cardiology and Other Societies on Cardiovascular Disease Prevention in Clinical Practice; European heart Journal; 33(13); pp. 1635-1701; Jul. 1, 2012.

Sun et al.: Characteristic wave detection in ECG signal using morphological transform; BMC cardiovascular disorders; 5(1); pp. 1-7; Dec. 2005.

Shvilkin et al.; U.S. Appl. No. 17/296,669 entitled "Hand held device for automatic cardiac risk and diagnostic assessment," filed May 25, 2021.

Vajdic et al.; U.S. Appl. No. 17/443,456 entitled "Electrocardiogram patch devices and methods," filed Jul. 26, 2021.

Goff et al.; 2013 ACC/AHA guideline on the assessment of cardiovascular risk: a report of the American College of Cardiology/ American Heart Association Task Force on Practice Guidelines; Journal of the American College of Cardiology;; 129(25 Suppl 2); pp. S49-S73; Jun. 2014.

Rakshit et al.; EKF with PSO technique for delineation of P and T wave in electrocardiogram (ECG) signal; in 2015 2nd International Conference on Signal Processing and Integrated Networks (SPIN); IEEE; pp. 696-701; Feb. 19, 2015.

Vajdic et al.; U.S. Appl. No. 17/609,014 entitled "Compact mobile three-lead cardiac monitoring device," filed Nov. 5, 2021.

Vajdic et al.; U.S. Appl. No. 17/570,368 entitled "Electrocardiogram patch devices and methods," filed Jan. 6, 2022.

\* cited by examiner

METHOD AND APPARATUS FOR RECONSTRUCTING ELECTROCARDIOGRAM (ECG) DATA

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are methods and apparatuses for generating electrocardiogram display data. More particularly, described herein are methods and apparatus (devices and systems) for generating 12-lead ECG display dataset based on captured 3-lead ECG data.

BACKGROUND

Acute Myocardial Infarction (AMI, also referred to as heart attack) remains a leading cause of mortality in the developed world. Finding accurate and cost-effective solutions for AMI diagnosis is vital. Survival of patients having AMI may depend critically on reducing treatment delay, and particularly reducing the time between symptom onset and medical treatment. A technology that would enable AMI diagnosis early after occurrence of AMI symptoms, for example, at patient's home or wherever the patient may be, may significantly decrease AMI mortality.

A 12-lead electrocardiogram (ECG) is a widely adopted tool used in cardiac diagnostics. In general, before ECG dataset is captured, characteristic points on patient's body are identified and electrodes are positioned with respect to these points. During ECG dataset capture, electrical voltages between two or more electrodes are measured, and corresponding ECG signals are called ECG leads. A conventional 12-lead ECG uses 10 electrodes to generate the 12 ECG signals or leads.

Recent advancements in the treatment of AMI and other cardiac disorders may include the use of a portable ECG device. In contrast to convention ECG equipment, the portable ECG devices may generate substantially few leads. For example, some portable ECG device may provide 3 leads.

However, since the conventional 12-lead ECG has been widely adopted, clinician analysis of ECG dataset other than the 12-lead ECG is difficult. Therefore, it may be advantageous to transform ECG dataset other than conventional 12-lead ECG dataset into a conventional 12-lead ECG format.

SUMMARY OF THE DISCLOSURE

The systems, methods, and devices of this disclosure each have several innovate aspects, no single one of which is solely responsible for the desirable attributes disclosed herein.

One innovative aspect of the subject matter described in this disclosure can be implemented as a method for synthesizing electrocardiogram (ECG) data. The method may include receiving a first 12-lead ECG dataset for a patient associated with a first dataset collection time, receiving a first 3-lead ECG dataset for the patient associated with a second dataset collection time different than the first dataset collection time (e.g., separated by more than an hour, more than a day, more than a week, etc.), determining a set of linear transformation parameters to synthesize 12-lead ECG dataset based at least in part on the first 12-lead ECG dataset and the first 3-lead ECG data, and synthesizing a second 12-lead ECG dataset from a second 3-lead ECG dataset associated with a third collection time based at least in part on the set of linear transformation parameters.

A method of generating electrocardiogram (ECG) data may include: receiving a current 3-lead ECG data recorded from a patient, wherein the current 3-lead ECG data comprises three orthogonal or pseudo-orthogonal leads; generating a derived 12-lead ECG dataset from the current 3-lead ECG data by applying a set of linear transformation parameters, wherein the set of linear transformation parameters are determined based at least in part on a prior 12-lead ECG dataset recorded from the patient at a first earlier collection time and a prior 3-lead ECG dataset recorded from the patient at a second earlier collection time that is different from the first earlier collection time, wherein the prior 3-lead ECG dataset is synchronized with the prior 12-lead ECG dataset by determining a representative beat for both the prior 3-lead ECG dataset and the prior 12-lead ECG dataset, wherein the set of linear transformation parameters comprises a set of transformation matrices that synthesize the prior 12-lead ECG dataset from the prior 3-lead ECG dataset; and outputting the derived 12-lead ECG dataset.

The prior 3-lead ECG dataset may be synchronized with the prior 12-lead ECG dataset by determining a representative beat that applies to both the prior 3-lead ECG dataset and the prior 12-lead ECG dataset. The representative beat may be representative of both the 12-lead ECG dataset and the 3-lead ECG dataset and may be the mean beat waveform (e.g., the component parts, such as the P, Q, R, S, and T segments (e.g., all or portion of the PR interval, all or portion of the QRS complex, all or portion of the ST segment, etc.). The representative beat may be identified as described herein, including by an arithmetic mean or average.

For example, a method of generating electrocardiogram (ECG) data may include: receiving a current 3-lead ECG data recorded from a patient, wherein the current 3-lead ECG data comprises three orthogonal or pseudo-orthogonal leads; generating a derived 12-lead ECG dataset from the current 3-lead ECG data by applying a set of linear transformation parameters, wherein the set of linear transformation parameters are determined based at least in part on a prior 12-lead ECG dataset recorded from the patient at a first earlier collection time and a prior 3-lead ECG dataset recorded from the patient at a second earlier collection time that is different from the first earlier collection time, wherein the prior 3-lead ECG dataset is synchronized with the prior 12-lead ECG dataset by determining a median beat for both the prior 3-lead ECG dataset and the prior 12-lead ECG dataset, segmenting each lead of the prior 12-lead ECG dataset and the prior 3-lead ECG dataset, wherein the set of linear transformation parameters comprises a set of transformation matrices that synthesize segments of the prior 12-lead ECG dataset from segments of the prior 3-lead ECG dataset; and outputting the derived 12-lead ECG dataset.

The prior 3-lead ECG dataset may be synchronized with the prior 12-lead ECG dataset by further determining a cross-correlation between the prior 3-lead ECG dataset and the prior 12-lead ECG dataset. The prior 3-lead ECG dataset may be synchronized with the prior 12-lead ECG dataset by further aligning features of a QRS complex of the prior 12-lead ECG dataset with features of a QRS complex of the prior 3-lead ECG dataset. The prior 3-lead ECG dataset may be synchronized with the prior 12-lead ECG dataset by further resampling at least one of the prior 12-lead ECG dataset and the prior 3-lead ECG dataset. The resampling may be in the frequency domain.

The prior 3-lead ECG dataset may be synchronized with the prior 12-lead ECG dataset by further determining the median beat for both the prior 3-lead ECG dataset and the prior 12-lead ECG dataset based on a plurality of heartbeats. The prior 3-lead ECG dataset may be synchronized with the prior 12-lead ECG dataset by further determining the median beat for both the prior 3-lead ECG dataset and the prior 12-lead ECG dataset by selecting a representative heartbeat from each of the prior 12-lead ECG dataset and the prior 3-lead ECG dataset.

Outputting the derived 12-lead ECG dataset may include displaying the derived 12-lead ECG dataset. As mentioned, the leads of the 3-lead ECG may be orthogonal or pseudo-orthogonal.

A method of generating electrocardiogram (ECG) data may include: receiving a current 3-lead ECG data recorded from a patient, wherein the current 3-lead ECG data comprises three orthogonal or pseudo-orthogonal leads; generating a derived 12-lead ECG dataset from the current 3-lead ECG data by applying a set of linear transformation parameters, wherein the set of linear transformation parameters are determined based at least in part on a prior 12-lead ECG dataset recorded from the patient at a first earlier collection time and a prior 3-lead ECG dataset recorded from the patient using orthogonal or pseudo-orthogonal leads at a second earlier collection time that is different from the first earlier collection time, wherein the prior 3-lead ECG dataset is synchronized with the prior 12-lead ECG dataset by determining a representative beat for both the prior 3-lead ECG dataset and the prior 12-lead ECG dataset, segmenting each lead of the prior 12-lead ECG dataset and the prior 3-lead ECG dataset, wherein the set of linear transformation parameters comprises a set of transformation matrices that synthesize segments of the prior 12-lead ECG dataset from segments of the prior 3-lead ECG dataset; and outputting the derived 12-lead ECG dataset.

Also described herein are methods for generating electrocardiogram (ECG) data that may include: accessing a first 12-lead ECG dataset for a patient associated with a first dataset collection time; accessing a first 3-lead ECG dataset for the patient associated with a second dataset collection time that is different from the first dataset collection time; determining a set of linear transformation parameters based at least in part on the first 12-lead ECG dataset and the first 3-lead ECG dataset; receiving a second 3-lead ECG dataset from a third time collection time; and outputting a second 12-lead ECG dataset synthesized from the second 3-lead ECG dataset using the set of linear transformation parameters.

In some variations, determining the set of linear transformation parameters may include synchronizing the first 3-lead ECG dataset with the first 12-lead ECG data. In some embodiments, the synchronizing may include determining a cross-correlation between the first 3-lead ECG dataset and the first 12-lead ECG data. In some other embodiments, the synchronizing may include resampling at least one of the first 12-lead ECG dataset and the first 3-lead ECG data. The resampling may be in the frequency domain.

In some variations, the synchronizing may include determining median beats for the first 12-lead ECG dataset and the first 3-lead ECG data. In some cases, determining the median beats may include determining an average or median value of each of the first 12-lead ECG dataset and the first 3-lead ECG dataset based on a plurality of heartbeats. In some other cases, determining the median beats may include selecting a representative heartbeat from each of the first 12-lead ECG dataset and the first 3-lead ECG data.

In some variations, determining the set of linear transformation parameters may include segmenting each lead of the first 12-lead ECG dataset and the first 3-lead ECG dataset and determining a set of transformation matrices to synthesize segments of the first 12-lead ECG dataset from segments of the first 3-lead ECG data.

In some variations, the method may include displaying the second 12-lead ECG data. In some other variations, determining the set of linear transformation parameters may include pre-processing the first 12-lead ECG dataset and the first 3-lead ECG data. In still other variations, the first 3-lead ECG may be orthogonal or pseudo-orthogonal. The resulting orthogonal or pseudo-orthogonal dataset may include dataset sufficient to determine associated conventional 12-lead ECG data.

Also described herein are ECG systems configured to perform any of these methods. These systems may be configured to determine the transformation matrix and/or form the 12-lead ECG from a currently recorded 3-lead (e.g. orthogonal or pseudo-orthogonal) ECG either locally (to the patient), remotely, or a combination of locally and remotely. For example, an ECG system may include a compute node configured to receive a first 12-lead ECG dataset for the patient associated with a first dataset collection time, receive a first 3-lead ECG dataset for the patient associated with a second dataset collection time different than the first dataset collection time, and determine a set of linear transformation parameters to synthesize 12-lead ECG dataset based at least in part on the first 12-lead ECG dataset and the first 3-lead ECG data. The ECG system may also include a portable ECG device configured to provide a second 3-lead ECG dataset from the patient, where the compute node is further configured to synthesize a second 12-lead ECG dataset from the second 3-lead ECG dataset associated with a third collection time based at least in part on the set of linear transformation parameters.

An electrocardiogram (ECG) system comprising: a portable ECG device configured to record a current 3-lead ECG dataset from a patient; and a non-transitory computer-readable storage medium comprising instructions that, when executed by one or more processors, cause the one or more processors to perform operations comprising: access a first 12-lead ECG dataset for the patient associated with a first dataset collection time; access a first 3-lead ECG dataset for the patient associated with a second dataset collection time different than the first dataset collection time; and determine a set of linear transformation parameters to synthesize 12-lead ECG dataset based at least in part on the first 12-lead ECG dataset and the first 3-lead ECG data, wherein the prior 3-lead ECG dataset is synchronized with the prior 12-lead ECG dataset by determining a representative beat for both the first 3-lead ECG dataset and the first 12-lead ECG dataset, wherein the set of linear transformation parameters comprises a set of transformation matrices that synthesize the first 12-lead ECG dataset from the first 3-lead ECG dataset; receive the current 3-lead ECG dataset from the portable ECG device; synthesize a second 12-lead ECG dataset from the current 3-lead ECG dataset based at least in part on the set of linear transformation parameters; and output the second 12-lead ECG dataset.

In some variations, the compute node may be further configured to synchronize the first 3-lead ECG dataset to the first 12-lead ECG data. The synchronization may include a determination of a cross-correlation between the first 3-lead ECG dataset and the first 12-lead ECG data. In some other variations, the synchronization may include an alignment of features of a QRS complex of the first 12-lead ECG dataset with features of a QRS complex of the first 3-lead ECG data. In still other variations, the synchronization may include a resampling of at least one of the first 12-lead ECG dataset and the first 3-lead ECG data. The resampling may be in the frequency domain.

In some variations, the synchronization may include a determination of median beats for the first 12-lead ECG dataset and the first 3-lead ECG data. In some cases, the determination of median beats may include a determination of an average or median value of each of the first 12-lead ECG dataset and the first 3-lead ECG dataset based on a plurality of heartbeats. In some other cases, the determination of median beats may include a selection of a representative heartbeat from each of the first 12-lead ECG dataset and the first 3-lead ECG data.

In some variations, the one or more processors (which may be referred to herein as a "compute node") may be further configured to segment each lead of the first 12-lead ECG dataset and the first 3-lead ECG dataset and determine a set of transformation matrices to synthesize segments of the first 12-lead ECG dataset from segments of the first 3-lead ECG data.

In some variations, the compute node may be further configured to generate display dataset based on the second 12-lead ECG data. In some other variations, the compute node may be further configured to pre-process the first 12-lead ECG dataset and the first 3-lead ECG data. In some variations, the first 3-lead ECG dataset may be orthogonal or pseudo-orthogonal dataset with respect to the first 12-lead ECG data. In some cases, the orthogonal or pseudo-orthogonal dataset may include dataset sufficient to determine associated conventional 12-lead ECG data.

Another innovative aspect of the subject matter described in this disclosure can be implemented as a non-transitory computer-readable storage medium comprising instructions that, when executed by one or more processors (e.g., of a compute node), cause the compute node to perform operations comprising receiving a first 12-lead ECG dataset for a patient associated with a first dataset collection time, receiving a first 3-lead ECG dataset for the patient associated with a second dataset collection time different than the first dataset collection time, determining a set of linear transformation parameters to synthesize 12-lead ECG dataset based at least in part on the first 12-lead ECG dataset and the first 3-lead ECG dataset and synthesizing a second 12-lead ECG dataset from a second 3-lead ECG dataset associated with a third collection time based at least in part on the set of linear transformation parameters.

For example, a non-transitory computer-readable storage medium comprising instructions that, when executed by one or more processors of one or more processors, cause the one or more processors to perform operations comprising: receiving a first 12-lead ECG dataset for a patient associated with a first dataset collection time; receiving a first 3-lead ECG dataset for the patient associated with a second dataset collection time different than the first dataset collection time; determine a set of linear transformation parameters based at least in part on the first 12-lead ECG dataset and the first 3-lead ECG data, wherein the first 3-lead ECG dataset is synchronized with the first 12-lead ECG dataset by determining a representative beat for both the first 3-lead ECG dataset and the first 12-lead ECG dataset, wherein the set of linear transformation parameters comprises a set of transformation matrices that synthesize the first 12-lead ECG dataset from the first 3-lead ECG dataset; receive a second 3-lead ECG dataset corresponding to the patient; synthesize a second 12-lead ECG dataset from the second 3-lead ECG dataset based at least in part on the set of linear transformation parameters; and output the second 12-lead ECG dataset.

In some variations, execution of instructions for determining the set of linear transformation parameters may cause the compute node to perform operations further comprising synchronizing the first 3-lead ECG dataset with the first 12-lead ECG data. In some cases, the synchronizing may include determining a cross-correlation between the first 3-lead ECG dataset and the first 12-lead ECG data. In some other cases, the synchronizing may include aligning features of a QRS complex of the first 12-lead ECG dataset with features of a QRS complex of the first 3-lead ECG data. In some embodiments, the synchronizing may include resampling at least one of the first 12-lead ECG dataset and the first 3-lead ECG data. In some cases, the resampling may be in the frequency domain.

In some variations, the synchronizing may include determining median beats for the first 12-lead ECG dataset and the first 3-lead ECG data.

BRIEF DESCRIPTION OF THE DRAWINGS

Novel features of embodiments described herein are set forth with particularity in the appended claims. A better understanding of the features and advantages of the embodiments may be obtained by reference to the following detailed description that sets forth illustrative embodiments and the accompanying drawings.

DETAILED DESCRIPTION

Electrocardiograms (ECGs) may graphically represent detected voltages associated with heart muscle contractions. The contractions, which are due to depolarization and repolarization of the heart muscle, may be studied by inspecting ECG graphs. A 12-lead ECG graph is a widely adopted tool that provides 12 different electrical voltage captures of detected heart voltages. Clinician have been widely trained at inferring heart conditions through studying a patient's 12-lead ECG data.

Portable ECG devices have been developed that allow the collection of ECG data in settings other than a clinic or a doctor's office. Many portable ECG devices, however, do not capture enough information to generate conventional 12-lead ECG data. For example, some portable ECG devices may only generate or capture 3-lead ECG data. Indeed, in some cases, patient records may only include 12-lead ECG data making interpretation of non 12-lead ECG data difficult.

Implementation of the subject matter described in this disclosure may be used to generate (synthesize) 12-lead ECG data from non-12-lead ECG data. More particularly, the subject matter may describe the synthesis of conventional 12-lead ECG data from 3-lead ECG data, such as orthogonal or pseudo-orthogonal 3-lead ECG data. In some variations, the synthesis/generation of the 12-lead ECG data may be based on applying transformation parameters to the 3-lead ECG data. The transformation parameters may be determined based on a patient's previously captured (recorded) 12-lead ECG data and the patient's 3-lead ECG data. Notably, the 12-lead ECG data may have been captured at a different time with respect to the 3-lead ECG data. In some variations, the transformation parameters may include one or more matrices that may be applied to 3-lead ECG data to synthesize related 12-lead ECG data. In this manner, a clinician may advantageously review 3-lead ECG data that may be presented as conventional 12-lead ECG data. In some cases, the 3-lead ECG data may be provided by a portable ECG device that may be used in settings other than a clinic, hospital, doctor's office or the like. For example, 3-lead ECG data may be captured by a patient at home, transmitted to a remote compute node and converted to conventional 12-lead ECG data. This 12-lead ECG data may be transmitted to a clinician and displayed.

The transformation parameters may be determined by synchronizing and segmenting the previously captured 12-lead ECG data and 3-lead ECG data. Next, least-squares analysis may be performed to deterministically determine a set of transformation matrices that may be used to synthesize 12-lead ECG data from 3-lead ECG data. Once determined, the transformation parameters may be stored. In some cases, the transformation parameters may be store remotely in a cloud-based storage system. 12-lead ECG data may be synthesized from 3-lead ECG data using these remotely stored transformation parameters.

Figure 1:
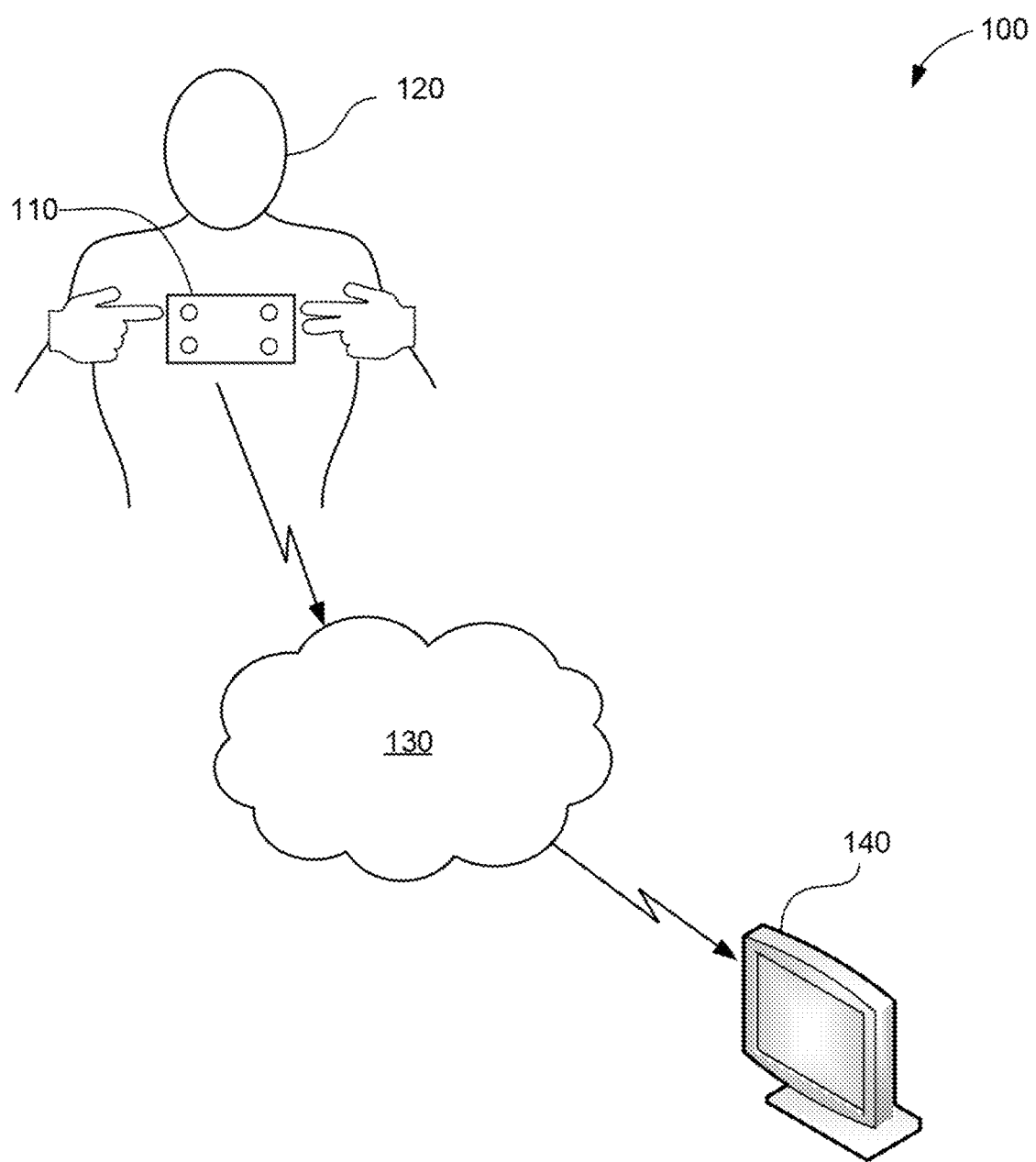
FIG. 1 shows one variation of an ECG system, in accordance with some embodiments.

FIG. 1 shows one variation of an ECG system 100, in accordance with some embodiments. The ECG system 100 may include a compact and portable ECG device 110 and a display device 140. The ECG device 110 may generate 3-lead ECG data for a patient 120. In some cases, the patient 120 may place the ECG device 110 on his or her chest while touching one or more contact electrodes with his or her hands. Furthermore, the ECG device 110 may also have multiple electrodes on a surface in contact with the patient 120. Thus, the ECG device 110 may contact the patient 120 with multiple electrodes through the patient's fingers and/or chest. Through the electrodes, the ECG device may generate the 3-lead ECG data. One example of an ECG device 110 is described in commonly owned U.S. Pat. No. 10,433,744, titled "MOBILE THREE-LEAD CARDIAC MONITORING DEVICE AND METHOD FOR AUTOMATED DIAGNOSTICS", filed on Apr. 11, 2016, which claims priority to U.S. provisional patent application No. 62/145,431, titled "MOBILE THREE-LEAD CARDIAC MONITORING DEVICE AND METHOD FOR AUTOMATED DIAGNOSTICS" and filed on Apr. 9, 2015.

These applications are herein incorporated by reference in their entirety.

In some variations, the leads generated by the ECG device 110 may be orthogonal or pseudo-orthogonal. The 3-lead ECG data from the ECG device 110 may include some or all of the information included in conventional 12-lead ECG data. However, some clinicians may be unfamiliar with interpreting cardiac data from the orthogonal or pseudo-orthogonal leads from the ECG device 110.

The data from the ECG device 110 may be transmitted to a network 130. The network 130 may include remote (cloud-based) storage and/or one or more remote compute nodes (not shown). In some variations, 12-lead ECG data may be synthesized from the 3-lead ECG data provided by the ECG device 110 within the network 130. The 12 lead ECG data may be displayed on the display device 140. In this way, a clinician may advantageously review the patient's ECG data in a conventional 12-lead format. Furthermore, the patient 120 may be located in a setting other than a clinic or doctor's office. Thus, the ECG device 110 may enable a clinician to remotely diagnose and treat a distant patient 120.

In some variations, the display device 140 may include one or more processors capable of synthesizing 12-lead ECG data from 3-lead ECG data. For example, the display device 140 may be a laptop computer, a smart display or monitor, a mobile phone, or any other feasible device. Thus, in some variations the network 130 may transmit the 3-lead ECG data from the ECG device 110 to the display device 140. The display device 140 may transform the 3-lead ECG data to 12-lead ECG data and then display this data.

Figure 2:
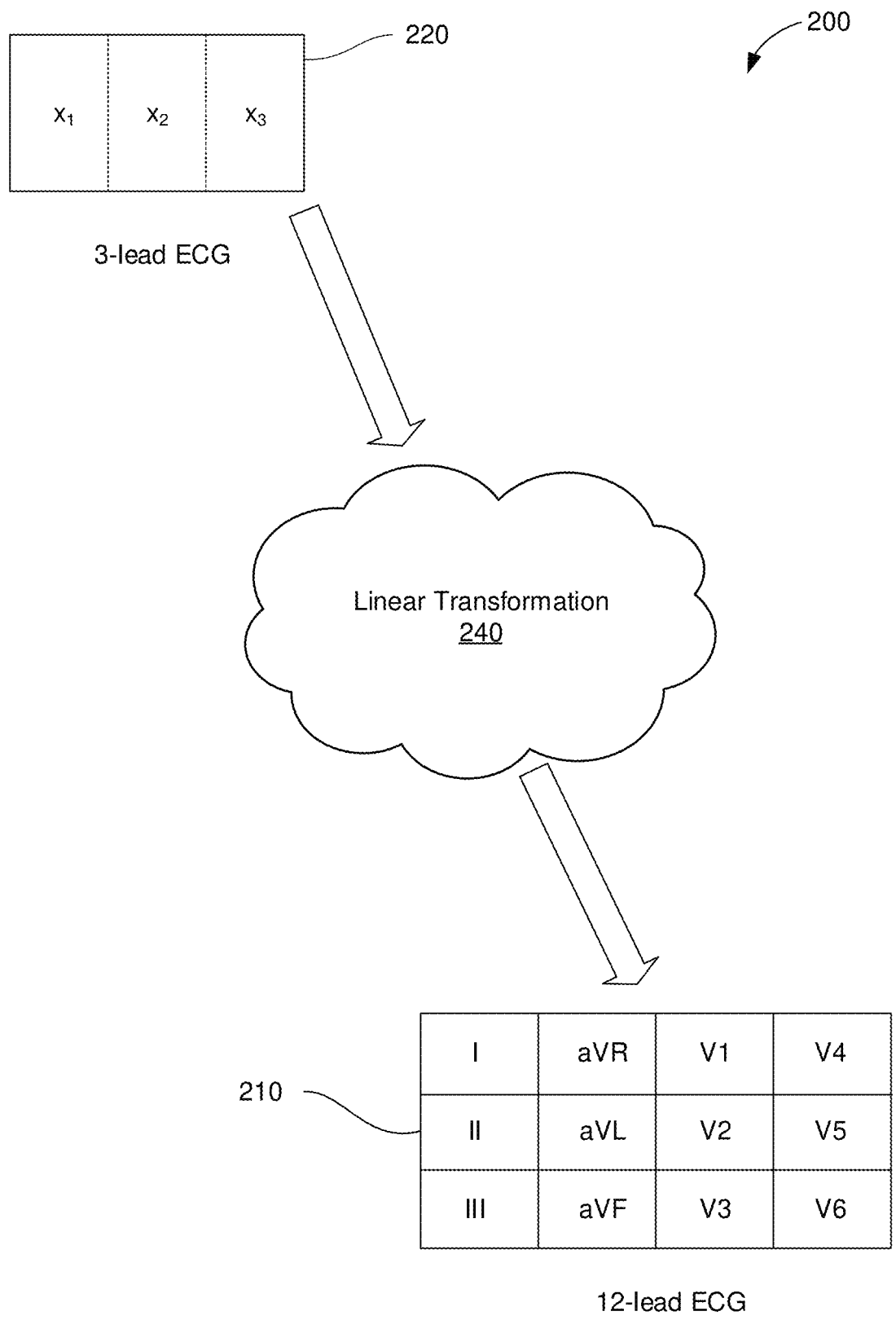
FIG. 2 is a simplified flow diagram illustrating the generation of 12-lead ECG dataset from a 3-lead ECG data.

FIG. 2 is a simplified flow diagram 200 illustrating the generation of 12-lead ECG data 210 from a 3-lead ECG data 220. In some variations, the 3-lead ECG data 220 may be provided by the ECG device 110 of FIG. 1. Although illustrated here as $X_1$, $X_2$, and $X_3$, the 3 leads from the ECG device 110 may have any feasible labels and, in some variations, may include more than 3 leads. The leads from the ECG device 110 may be orthogonal or pseudo-orthogonal with respect to a lead-space encompassing a conventional 12-lead ECG such as the 12-lead ECG data 210. Thus, most or all of the information that may be included in a conventional 12-lead ECG may be included (encoded) in the orthogonal or pseudo-orthogonal leads from the ECG device 110. In other words, the orthogonal or pseudo-orthogonal data includes data sufficient to determine the conventional 12-lead ECG data. Although the 12 leads are labeled I, II, III, aVR, aVL, aVF, V1, V2, V3, V4, V5, and V6, the leads of the 12-lead ECG data 210 may have any feasible label. In some variations more or few leads may be generated from the 3-lead ECG data 220.

In some embodiments, the 3-lead ECG 220 data may be processed with a linear transformation 240 that may generate or synthesize the 12-lead ECG data 210. Thus, the 3-lead ECG data 220 from the ECG device 110 may be transformed into 12-lead ECG data 210 that may be more easily interpreted by clinicians due to the widely adopted and understood nature of conventional 12-lead ECG data. In some cases, the synthesized 12-lead ECG data 210 may be displayed as conventional 12-lead ECG charts for analysis and review by clinicians.

In some variations, the linear transformation 240 may be based, at least in part, on a patient's 12-lead ECG data (not shown) that may have been previously captured (recorded) and stored. The relationship between the linear transformation 240 and a patient's previous 12-lead ECG data is illustrated graphically in FIG. 3.

Figure 3:
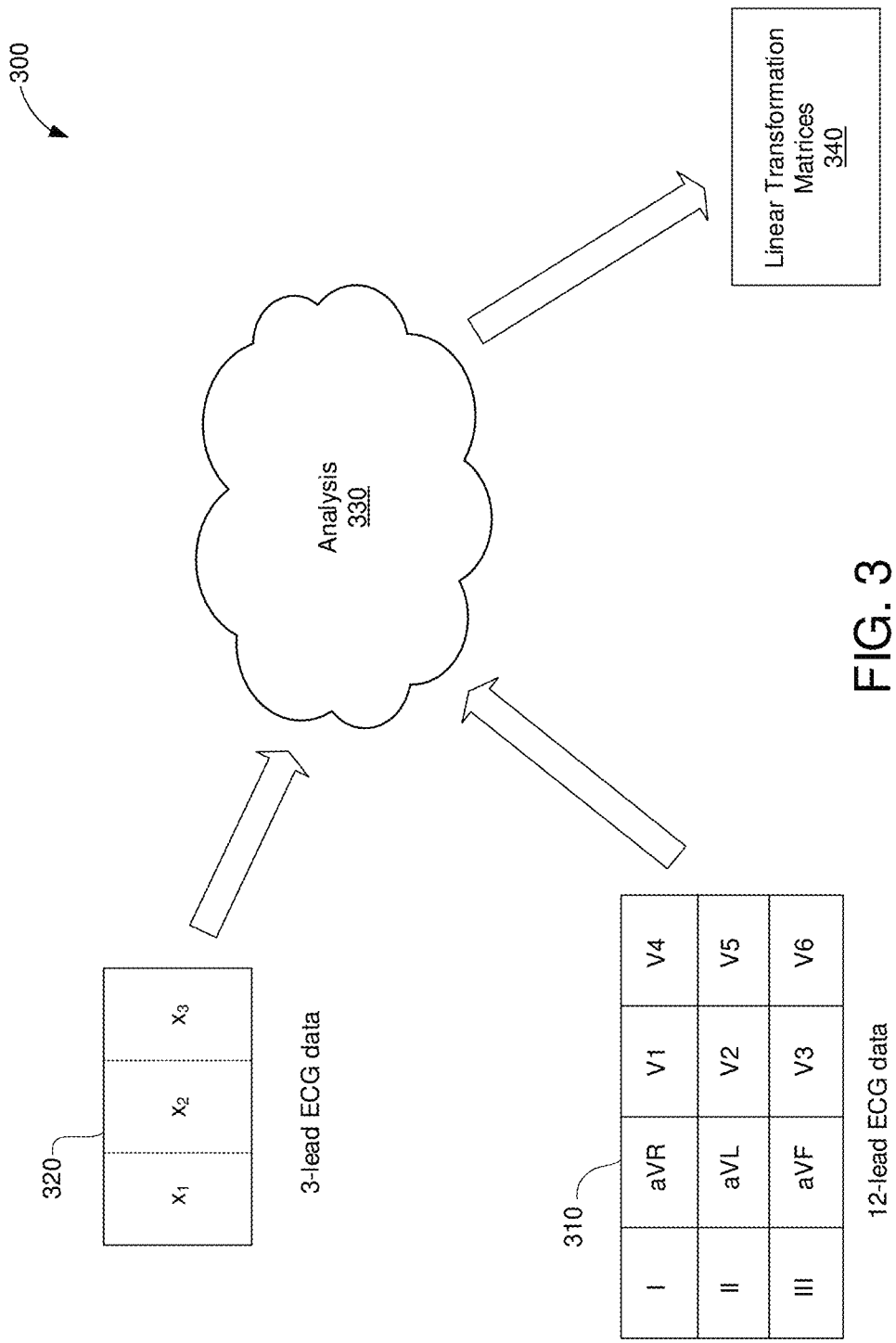
FIG. 3. graphically shows a process flow for synthesizing 12-lead ECG dataset based on 3-lead ECG data.

FIG. 3. graphically shows a process flow 300 for determining or synthesizing 12-lead ECG data based on 3-lead ECG data. Although described with respect to 3-lead ECG data, the process described herein may be adapted for use with any feasible ECG data that is different than the conventional 12-lead ECG data.

The process flow 300 may use a patient's 12-lead ECG data 310 that has been previously recorded and/or captured and the patient's 3-lead ECG data 320. The 12-lead ECG data 310 may be from any feasible ECG device capable of generating and/or recording 12-lead ECG data. In some variations, the 12-lead ECG data 310 may be a baseline ECG recording with respect to a patient's known physical state. In some cases, the 12-lead ECG data 310 may be from health records associated with the patient. For simplicity, the 12-lead ECG data 310 is shown to include I, II, III, aVR, aVL, aVF, V1, V2, V3, V4, V5, and V6 leads, but in other embodiments, the 12-lead ECG data 310 may include any feasible leads.

The 3-lead ECG data 320 may include any feasible 3-lead orthogonal or pseudo-orthogonal ECG data. In some variations, the 3-lead ECG data 320 may be provided by a compact/portable ECG device, such as the ECG device 110 of FIG. 1. For simplicity, the 3-lead ECG data 320 is shown to include $X_1$, $X_2$, and $X_3$ leads, but any feasible 3-lead ECG data may be included. Notably, the 12-lead ECG data 310 and the 3-lead ECG data 320 may be collected (e.g., captured or recorded) at different times. In other words, the 12-lead ECG data 310 may be collected/recorded at a first time and the 3-lead ECG data 320 may be collected/recorded a second time that is different from the first time.

The 12-lead ECG data 310 and the 3-lead ECG data 320 may undergo an analysis 330 to determine a relationship between the two. In some cases, the analysis 330 may determine a linear relationship between the 3-lead ECG data 320 and the 12-lead ECG data 310. In some variations, the linear relationship may include one or more linear transformation matrices 340 that may be used to transform 3-lead ECG data 320 to 12-lead ECG data (not shown). In other words, the linear transformation matrices 340 may be used to synthesize and/or display 12-lead ECG data derived from 3-lead ECG data 320. In this manner, a patient's 3-lead ECG data 320 may be presented as a conventional 12-lead ECG data enabling a clinician to diagnose the patient's cardiac health. In some cases, the 3-lead ECG data 320 may be provided by the patient in a home setting or otherwise away or separated from traditional medical facilities. For example, the patient may collect the 3-lead ECG data 320 with the ECG device 110 at home. Thus, extended cardiac care may be provided to patients distant or separated from specialized cardiac care facilities.

Figure 4:
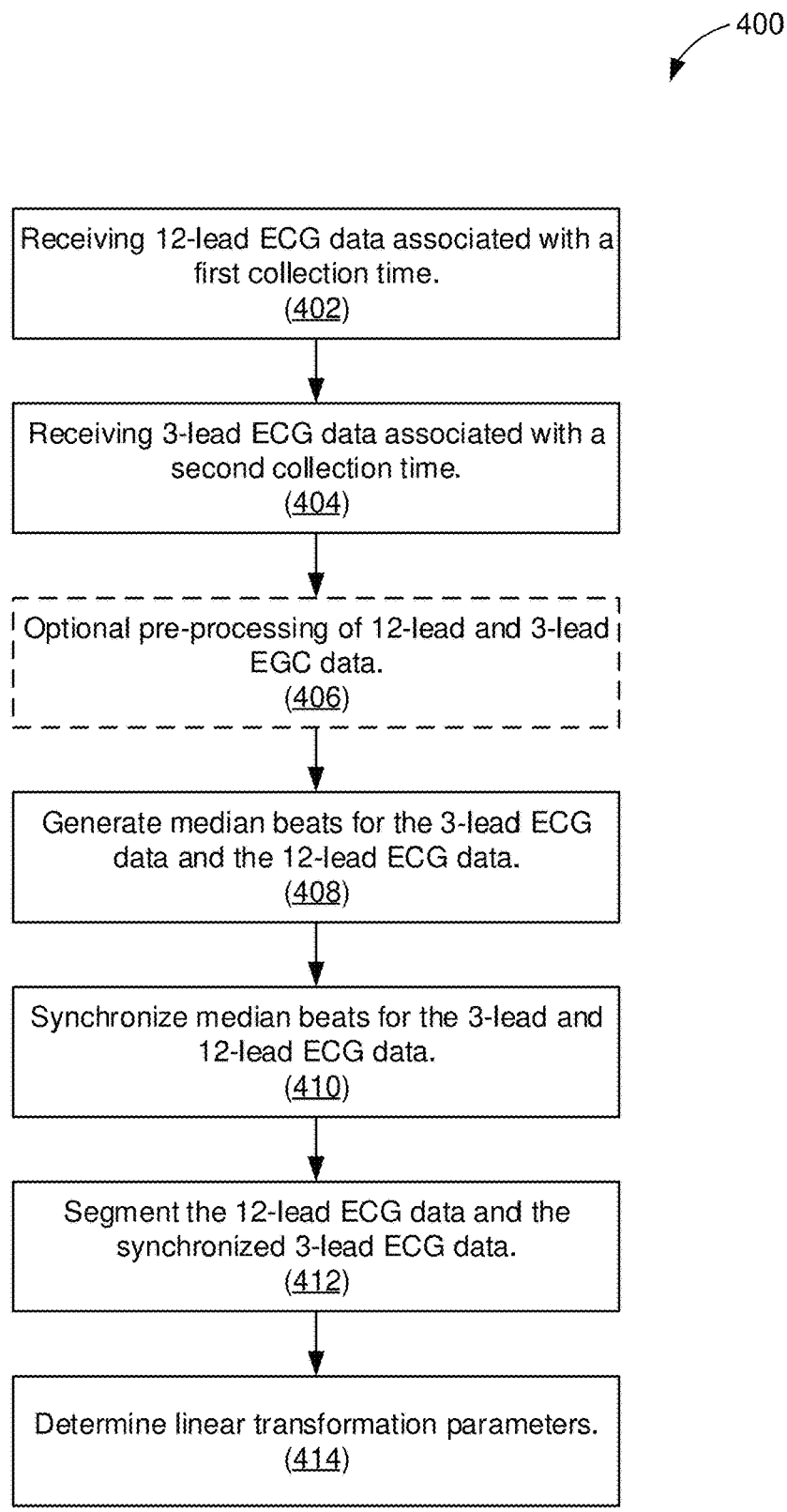
FIG. 4 is a flowchart depicting an example method for determining linear transformation matrices, in accordance with some embodiments.

FIG. 4 is a flowchart depicting an example method 400 for determining linear transformation matrices, in accordance with some embodiments. Some examples may perform the operations described herein with additional operations, fewer operations, operations in a different order, operations in parallel, and some operations differently. The method 400 may be performed in conjunction with one or more processors locally (with respect to the patient) or remotely by a processor or computer, such as a cloud-based processing node. In other variations, the method 400 may be performed by any other suitable system or device.

The method 400 may sometimes be associated with a "calibration phase" during which the linear transformation matrices are "calibrated" to transform 3-lead ECG data to 12-lead ECG data. As an overview to the process, 12-lead ECG data that was recorded/captured at a first time is aligned to 3-lead ECG data that was recorded/captured at a second time. After alignment, the ECG data is segmented, and transformation matrices associated with the ECG data segments are determined.

The method 400 begins in block 402 where a patient's 12-lead ECG data associated with a first collection time (e.g., a data collection time) is received. The 12-lead ECG data may be collected and/or recorded with any feasible ECG equipment. In some variations, the 12-lead ECG data may be received from health care records, including electronic health care records. In some cases, the 12-lead ECG data may be stored in one or more remote file systems, such as cloud-based systems. Thus, the 12-lead ECG data may be accessed through one or more networks including, for example, the internet. As noted, the 12-lead ECG data may be associated with a first collection time. That is, the 12-lead ECG data may be captured and/or recorded with respect to a first time or time period.

Next, in block 404, the patient's 3-lead ECG data associated with a second collection time is received. The 3-lead ECG data may be collected and/or recorded by any feasible ECG equipment, such as the ECG device 110 of FIG. 1. The 3-lead ECG data may be orthogonal or pseudo-orthogonal ECG data and may be captured and/or recorded with respect to a second time or time period. Notably, the first time or time period may be different than the second time or time period. In some cases, the 3-lead ECG data may be stored on a remote file system and accessed through one or more networks.

Next, in block 406, the 12-lead ECG data and the 3-lead ECG data may be pre-processed. This operation may be optional, as illustrated with dashed lines in FIG. 4. Signal pre-processing may include noise filtering, baseline wandering removal, or any other feasible pre-processing operations. For example, pre-processing operations for the 12-lead ECG data and/or the 3-lead ECG data may include low-pass filtering to bandwidth limit the respective data signals and remove out-of-band noise.

Next, in block 408, median beats are generated for the 3-lead ECG data and the 12-lead ECG data. In some embodiments, a median beat may be generated for each lead of the associated ECG data. To generate a median beat, different beats of a particular lead of ECG data are aligned. In some cases, the alignment may be determined by a cross-correlation of QRS complexes included in the heartbeat of the selected lead. After the ECG data of the selected lead is aligned, then median values associated with the particular ECG lead may be determined to determine the median beat. Although described herein as a median operation, in some other embodiments, any other feasible selection operation may be used including, but not limited to, a mean operation, a mode operation, or the like. In some variations, instead of determining a median beat for each ECG data lead, a representative lead (e.g., a representative heartbeat) may be selected.

Next, in block 410, the median beats for the 3-lead and 12-lead ECG data are synchronized. Since the 12-lead ECG data may have been captured at a different time than the 3-lead ECG data, the time periods of the 12-lead ECG data may be different than the time periods of the 3-lead ECG data. Thus, prior to determining any ECG data relationships, the 3-lead ECG data should be synchronized and/or normalized with respect to the 12-lead ECG data. In some variations, the ECG data may be synchronized with respect to intervals. For example, the ECG data may be synchronized with respect to depolarization intervals and with respect to repolarization intervals.

Figure 5:
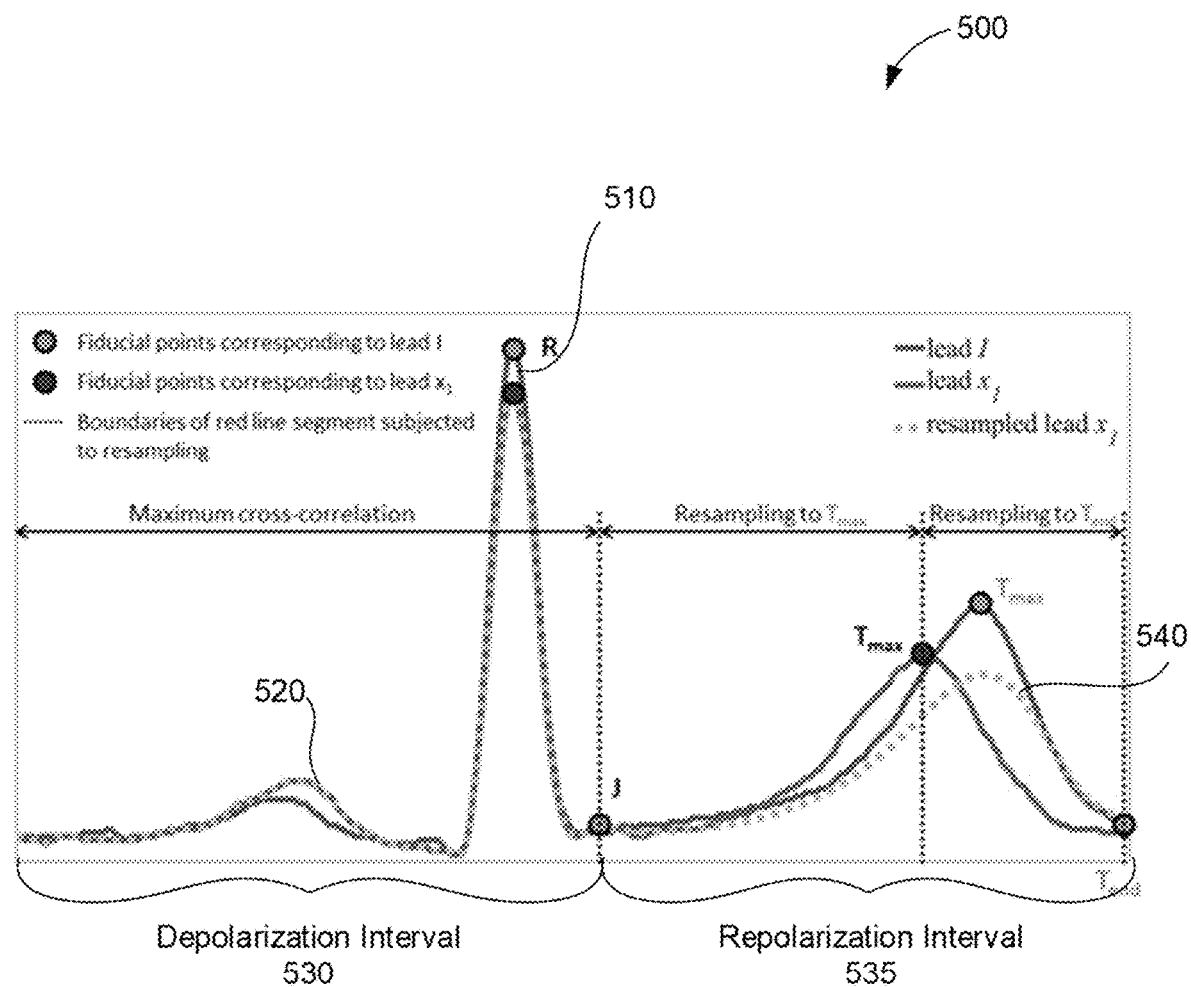
FIG. 5 is a lead diagram that includes lead I from a 12-lead ECG and an $X_1$ lead from a 3-lead ECG, in accordance with some embodiments.

FIG. 5 is a lead diagram 500 that includes lead I 510 from a 12-lead ECG and an $X_1$ lead 520 from a 3-lead ECG, in accordance with some embodiments. A depolarization interval 530 may begin with atrial depolarization (e.g., a beginning of a heartbeat when atria contract) and may end after the QRS complex (depicted as point J in the lead diagram 500). In some embodiments, synchronization of the ECG data with respect to the depolarization intervals may include cross-correlation of a first ECG data lead with a second ECG data lead. For example, the cross-correlation may be used to align the I lead 510 with the $X_1$ lead 520 by using distinct features of the QRS complex included in each ECG data lead. In some variations, the synchronization may include a determination of a time shift between the I lead 510 and the $X_1$ lead 520. After the determination of the time shift, the other leads of the 3-lead ECG (e.g., the $X_2$ and the $X_3$ leads, not shown here for simplicity) may be shifted by the same or a similar amount.

A repolarization interval 535 may begin at the J point and extend to the end of the heartbeat. Synchronization during the repolarization interval 535 may include resampling the shorter (in time) ECG lead to be closer in length to the longer ECG lead. The portion of the ECG leads after the point J may be divided into two sections. The first section begins at the point J and extends to $T_{max}$. ($T_{max}$ may be a relative maximum after the point J.) The second section begins at $T_{max}$ and extends to the end of the heartbeat, $T_{end}$.

First, the length of the $X_1$ lead 520 is compared to the length of the I lead 510 within the interval between point J to $T_{max}$. The shorter ECG is resampled so that its length is extended to approximately match that of the longer ECG. In the example of FIG. 5, the length of the I lead 510 from the point J to $T_{max}$ is longer than the respective length of the $X_1$ lead 520. Thus, the $X_1$ lead 520 may be resampled to approximately match the length of the I lead 510 between point J and $T_{max}$.

In some variations, the resampling of the ECG leads may occur in the frequency domain by adding zero samples to the shorter lead. For example, if the section of the I lead 510 between the point J and $T_{max}$ has M samples and the equivalent section of the $X_1$ lead 520 has N samples, then M-N zero-valued samples may be added to the center of the frequency spectrum of the $X_1$ lead 520 before transforming back to the time domain. In some other variations, the resampling may occur in the time domain.

The second section (between $T_{max}$ and $T_{end}$) of the $X_1$ lead 520 and the second section of I lead 510 may be resampled in the same of a similar manner. The resampled ECG lead may be filtered by fitting to a polynomial, such as a $10^{th}$ order polynomial, to reduce noise. A resulting resampled and filtered $X_1$ lead 540 is shown in FIG. 5 for reference. The same resampling operations may be performed with respect to the $X_2$ and the $X_3$ ECG leads.

Returning to the FIG. 4, in block 412, the median beat of the 12-lead ECG data and the synchronized 3-lead ECG data are divided into a number of segments. In some variations, the 12-lead and 3-lead ECG data may be divided into three segments, however other numbers of segments are possible. The segments may be based on fiducial points that may be identified on each ECG lead. In some variations, the fiducial points of $P_{start}$, Q, J, and $T_e$nd may be used.

Figure 6:
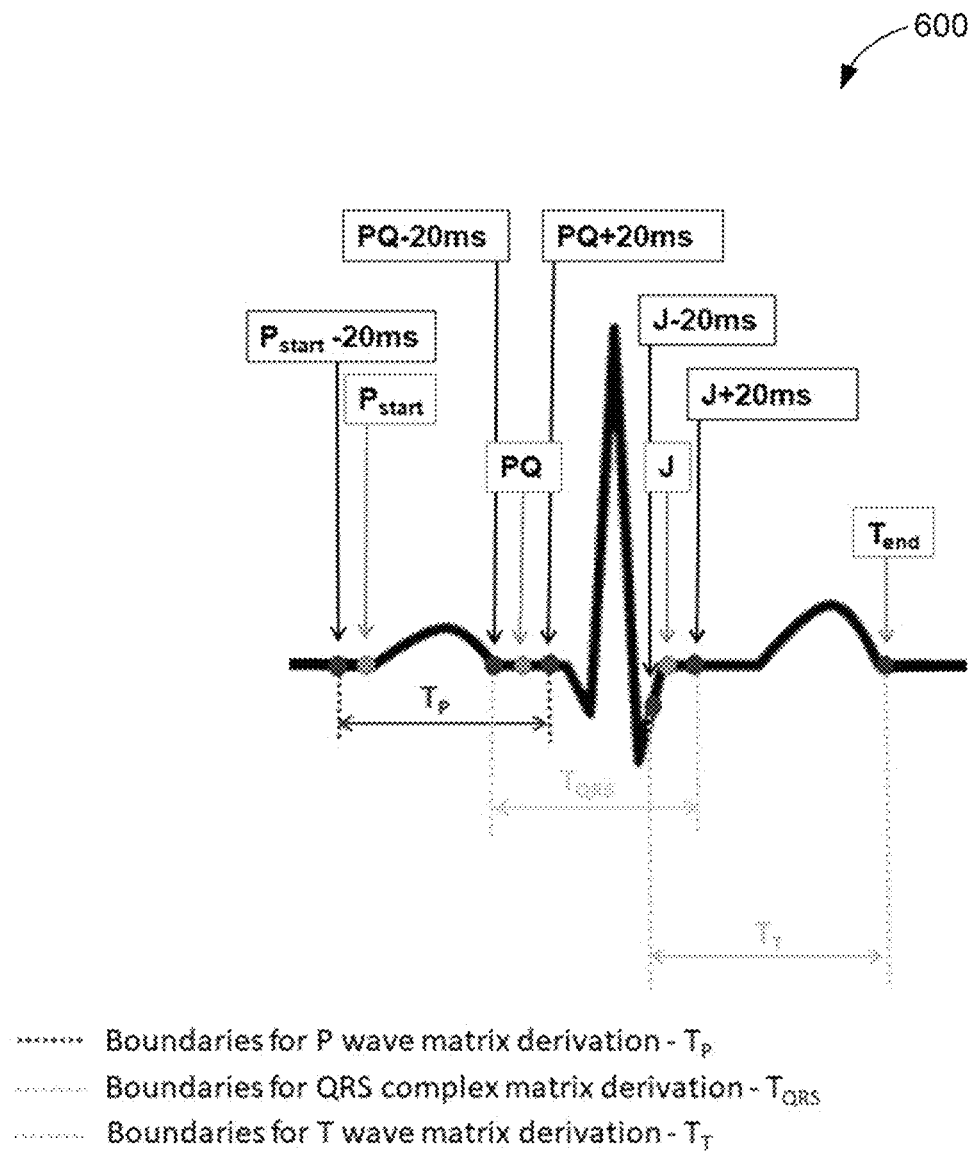
FIG. 6 is a diagram showing some fiducial points with respect to an example ECG lead.

FIG. 6 is a diagram 600 showing some fiducial points with respect to an example ECG lead. $P_{start}$ may refer to a beginning the ECG lead. Notably, the $P_{start}$ fiducial occurs before the P-wave which is a first positive ECG deflection within a heartbeat period illustrated in FIG. 6. The Q fiducial is associated with the beginning of the QRS complex portion of the ECG lead. The QRS complex includes the Q, R, and S waves and is associated with the contraction of the ventricles of the heart. The J fiducial is associated with the end of the QRS complex. The $T_e$nd fiducial is the end of the ECG lead.

In some variations, the fiducial points may be automatically determined, for example by computer algorithms or programs executed by one or more processors. Example methods are discussed by Sun, Y et. al. (2005). Characteristic wave detection in ECG signal using morphological transform. BMC Cardiovasc Disord, September 20; 5:28 and Rakshit, M et. al. (2015). EKF with PSO technique for delineation of P and T wave in electrocardiogram (ECG) signal. $2^{nd}$ International Conference on Signal Processing and Integrated Networks (SPIN), IEEE.

Additionally, a PQ fiducial point may be determined. The PQ fiducial point is located in the interval between [Q−60 milliseconds (ms), Q−20 ms]. Note that Q is associated with the beginning of the Q wave of the QRS complex described above. The PQ fiducial point is based on a minimum value of the 3-lead ECG data during the [Q−60 ms, Q−20 ms] interval. The minimum value may be based on a vector magnitude of the orthogonal or pseudo-orthogonal leads and may $$V_m = \sqrt{x_1^2 + x_2^2 + x_3^2}.$$

be expressed as

Based on the determined fiducial points, three segments may be determined for each ECG lead. Example segments may include a first segment ($T_P$) defined as [$P_{start}$−20 ms, PQ+20 ms], a second segment ($T_{QRS}$) defined as [PQ−20 ms, J+20 ms], and a third segment ($T_T$) defined as [J−20 ms, $T_{end}$]. Example segments $T_P$, $T_{QRS}$, and $T_T$ are shown in FIG. 6 for reference. In some embodiments, the three segments may overlap. Overlapping segments may enable later determined transformation functions and/or matrices to smooth discontinuities between segments Next, in block 414, patient-specific transformation parameters are determined with respect to the determined segments. In some variations, the transformation parameters may be expressed as linear transformation matrices (e.g., linear transformation parameters). Four transformation matrices may be defined: One transformation matrix may be associated with each segment defined in block 412 (e.g., $T_P$, $T_{QRS}$, and $T_T$ segments) and a fourth matrix associated with a transition region between the QRS complex and the T wave.

In some variations, matrices associated with the $T_P$, $T_{QRS}$, and $T_T$ segments may be denoted as $T_P$, $T_{QRS}$, $T_T$. These matrices may be defined as $$T_k = X^\dagger_k * Y_k \quad \text{(eq. 1)}$$

where: † is the Moore-Penrose pseudo-inverse operator (i.e., $X^\dagger_k = (X^T_k * X_k)^{-1} * X^T_k$;
X=($X_1$, $X_2$, $X_3$) are the leads from the 3-lead ECG synchronized to the 12-lead ECG;
Y=($Y_1$, $Y_2$ ... $Y_{12}$) are the leads from the 12-lead ECG; and
k=P, QRS, or T segments.

In some embodiments, the Y vector may include 8 independent leads and 4 other leads based on $Y_1$ and $Y_2$ limb leads. In some other embodiments, the transformation matrices may be calculated using a least squares method. For example:

$$T_k = (X_k^T * W * X_k)^{-1} * X_k^T * W * Y_k \quad \text{(eq. 2)}$$

where W is a diagonal matrix containing weights for each sample within segment k:

$$W = \begin{bmatrix} W_{1,k} & 0 & 0 \\ 0 & \cdots & 0 \\ 0 & 0 & W_{n,k} \end{bmatrix};$$

n is a number of samples within segment k; and
$W_{i,k}$ (for i=1 . . . n) is a weight for the i-th sample calculated as $$W_{i,k} = \sqrt{x_{1,i,k}^2 + x_{2,i,k}^2 + x_{3,i,k}^2}$$

In some variations, a number of heartbeats for each lead beat may be concatenated and then the above equation (equation 2) applied. For example, five or more beats may be concatenated, however, any number of beats may be used, including 1.

In some other variations, equation 2 may be applied separately to each heartbeat j, thereby forming a collection of matrices $\{T_{Pj}\}$, $\{T_{QRSj}\}$, and $\{T_{Tj}\}$. Then, a median value for each set of respective coefficients within each collection of matrices may be calculated.

A fourth matrix may be used to synthesize the region between the QRS complex and the T-wave. This region is sometimes referred to as the "ST segment" referencing the segment between conventional S and T waves on an ECG trace. In some variations, a transient matrix $T_{transient}$ may be a weighted combination of $T_{QRS}$ and $T_T$ matrices as expressed below in equation 3:

$$T_{transient} = T_{QRS} + \frac{P_{j,T}}{P_{j,QRS} + P_{j,T}} (T_T - T_{QRS}) \quad \text{(eq. 3)}$$

where: $P_{j,QRS}$ and $P_{j,T}$ represent a power associated with the QRS and T segments with respect to the j-th heartbeat $$P_{j,k} = \sqrt{\sum_{i=1}^{N_{j,k}} (x_{1,i}^2 + x_{2,i}^2 + x_{3,i}^2)} \quad \text{(eq. 4)}$$

T, QRS;
i= is a sample number (such that i=1, 2, . . . Nj,k);
Nj,k is a total number of samples for the j-th heartbeat and segment k; and
$x_1$, $x_2$, and $x_3$ are values for the leads of the 3-lead ECG of the segment k and the j-th heartbeat.

Thus, the linear transformations $T_P$, $T_{QRS}$, $T_T$, and $T_{transient}$ may generate (as outputs) 12-lead ECG data based on 3-lead ECG data (as inputs). In particular, the linear transformations may generate/synthesize segments of the 12-lead ECG data based on segments of the 3-lead ECG data. In some embodiments, the segments of the 12-lead ECG data may overlap. The overlap may help smooth discontinuities within the generated (synthesized) 12-lead ECG data.

The linear transformations $T_P$, $T_{QRS}$, $T_T$, and $T_{transient}$ may be stored for later use. For example, the linear transformations may be used to synthesize 12-lead ECG data based on 3-lead ECG data that has been recorded/captured at a later time with respect to the 3-lead ECG data that has been used to determine the linear transformations. In some embodiments, the transformations may be stored in cloud storage, or within any feasible medium.

The synthesized 12-lead ECG data may include ECG display data. Thus, in some embodiments the 12-lead ECG display data may be displayed to a clinician thereby enabling the clinician to provide a cardiac examination and diagnosis for a patient based on 3-lead ECG data. In other words, the 3-lead ECG data may be advantageously transformed into conventional appearing 12-lead ECG data to enable cardiac examination.

Figure 7:
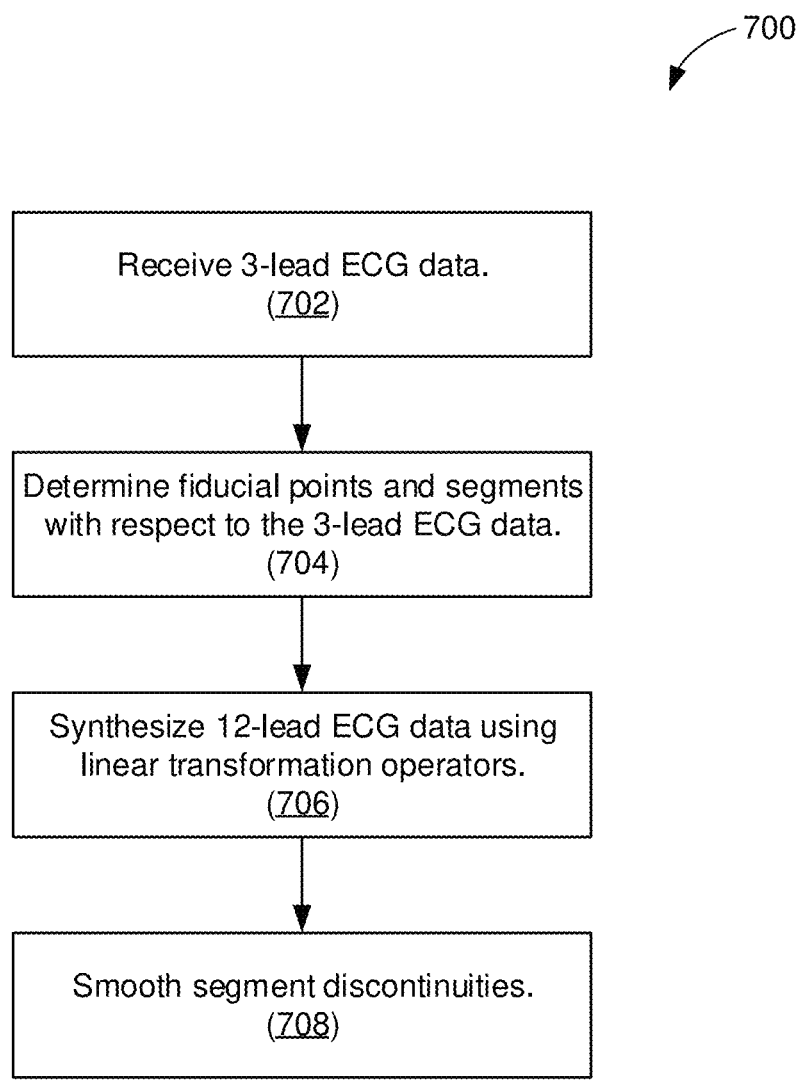
FIG. 7 is a flowchart depicting an example method for synthesizing 12-lead ECG dataset from 3-lead ECG data, in accordance with some embodiments.

FIG. 7 is a flowchart depicting an example method 700 for synthesizing 12-lead ECG data from 3-lead ECG data, in accordance with some embodiments. In some variations, the 3-lead ECG data may include orthogonal or pseudo-orthogonal ECG lead data. The method 700 may sometimes be referred to as a "monitoring phase" during which the transformation matrices (determined with respect to the method 400) are used to synthesize 12-lead ECG data that may be displayed and reviewed by a clinician.

The method 700 begins in block 702 where 3-lead ECG data is received. In some variations, the 3-lead ECG data may be provided (received from) by the ECG device 110 of FIG. 1. In other variations, the 3-lead ECG data may be provided by a remote server such as a cloud-based storage device. In some variations, the 3-lead ECG data may be orthogonal or pseudo-orthogonal ECG data (as described with respect to FIG. 2). Next, in block 704, fiducial points and fiducial related segments are determined with respect to the 3-lead ECG data. In some embodiments, the fiducial points may include $P_{start}$, Q, J, and $T_{end}$ points and may be determined as described above with respect to FIG. 4. Based on these fiducial points, four synthesis segments may be defined. The four segments may correspond to the $T_P$, $T_{QRS}$, $T_T$ and $T_{transient}$ segments described above with respect to FIG. 4.

Next, in block 706, 12-lead ECG data is synthesized from the received 3-lead ECG data for each of the above-defined segments. In some embodiments, the linear transformations described with respect to FIG. 4 (e.g., the linear transformation matrices $T_P$, $T_{QRS}$, $T_T$, and $T_{transient}$) may be used to synthesize each segment of the 12-lead ECG data. For example, the $T_P$ segment may be synthesized (e.g., determined or reconstructed) by matrix multiplication of the received 3-lead ECG data and the $T_P$ matrix. The $T_{QRS}$ segment may be synthesized by matrix multiplication of the received 3-lead ECG data by the $T_{QRS}$ matrix. The $T_T$ segment may be synthesized by matrix multiplication of the received 3-lead ECG data by the $T_T$ matrix. The ST segment may be synthesized by a weighted combination of the $T_{transient}$, $T_{QRS}$, and $T_T$ matrices expressed below by equation 5:

$$(x_{1,i}, x_{2,i}, x_{3,i})_{synth} = (x_{1,i}, x_{2,i}, x_{3,i})[J_k - 20 \text{ ms}, J_k]*$$
$$(w*T_{QRS}V*T_{transient}) + (x_{1,i}, x_{2,i}, x_{3,i})[J_k, J_k + 80 \text{ ms}]*$$
$$(Z*T_{transient} + q*T_T) \quad \text{(eq. 5)}$$

where: i= is a sample number and ranges from 1, 2, . . . $N_k$;
$N_k$ is the total number of samples for the k-th heartbeat;
$x_{1,k}$, $x_{2,k}$, and $x_{3,k}$ are values for the 3-lead ECG during the ST segment for the k-th heartbeat; and
w,v,z, and q are arbitrarily chosen weighting coefficients.

In some embodiments, the ST segment may be defined within the [J−20 ms, J+80 ms] interval. In some cases, with some weighting coefficients, the reconstruction matrix may be simplified to a single matrix, $T_{single}$, the matrix $T_T$, and the matrix $T_{QRS}$. In another embodiment, the ST segment may be reconstructed with a population matrix, $T_{POP}$.

Next, in block 708, discontinuities between the synthesized segments are smoothed. In some cases, the smoothing is obtained by transitioning between matrices used in block 706 instead of abruptly changing between matrices. One example is expressed below in equation 6:

$$T_i = T_{i,k} + \frac{i + tp_{k+1}/2}{tp_{k+1}}(T_{i,k+1} - T_{i,k}) \quad \text{(eq. 6)}$$

where: Ti is a transient matrix applied to an i-th sample within a transient period;
k refers to $T_P$, $T_{QRS}$, $T_T$, and $T_{transient}$ segments;
i=$tp_{k+1}/2, \ldots, -1, 0, 1, \ldots, tp_{k+1}/2$ is the sample number calculated from the beginning of segment k+1; and
tpK+1 is a transition period.

In some variations, discontinuities that occur between segments of the synthesized 12-lead ECG signals may be smoothed using one or more cubic-spline functions. Furthermore, although described as synthesizing 12 leads of a 12-lead ECG, the method of FIG. 7 may be used to synthesize fewer than 12-leads. For example, the method of FIG. 7 may be used to synthesize a subset of the 12 conventional ECG leads. In yet another variation, the methods described herein may be used to synthesize or reconstruct a missing lead of any well-defined set of ECG leads. In this case, the base or orthogonal/pseudo-orthogonal leads can be any leads for which the missing ECG leads may be related.

Figure 8:
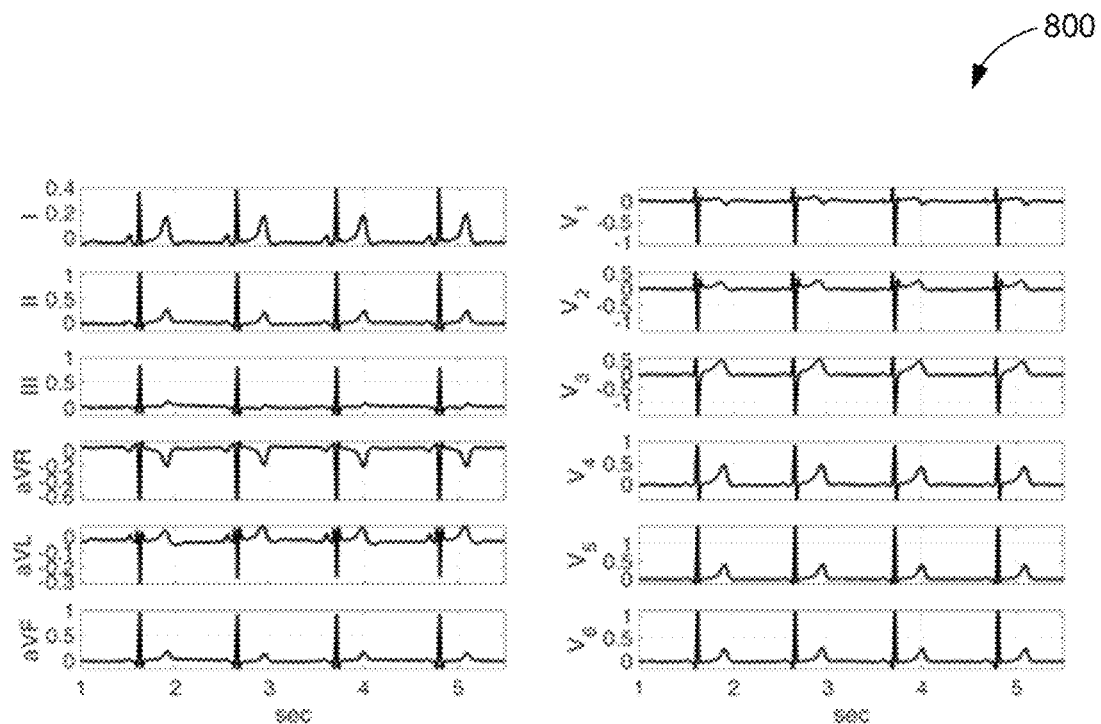
FIG. 8 is a graph of an example 12-lead ECG, in accordance with some embodiments.

FIG. 8 is a graph of an example 12-lead ECG data 800, in accordance with some embodiments. The 12-lead ECG data 800 that may be captured (recorded) at a first collection time. As shown, the 12-lead ECG data 800 may include the 12 conventional leads of I, II, III, aVR, aVL, aVF, $V_1$, $V_2$, $V_3$, $V_4$, $V_5$, and $V_6$. The 12-lead ECG data 800 may be used to determine linear transformation parameters as described with respect to FIG. 4.

Figure 9:
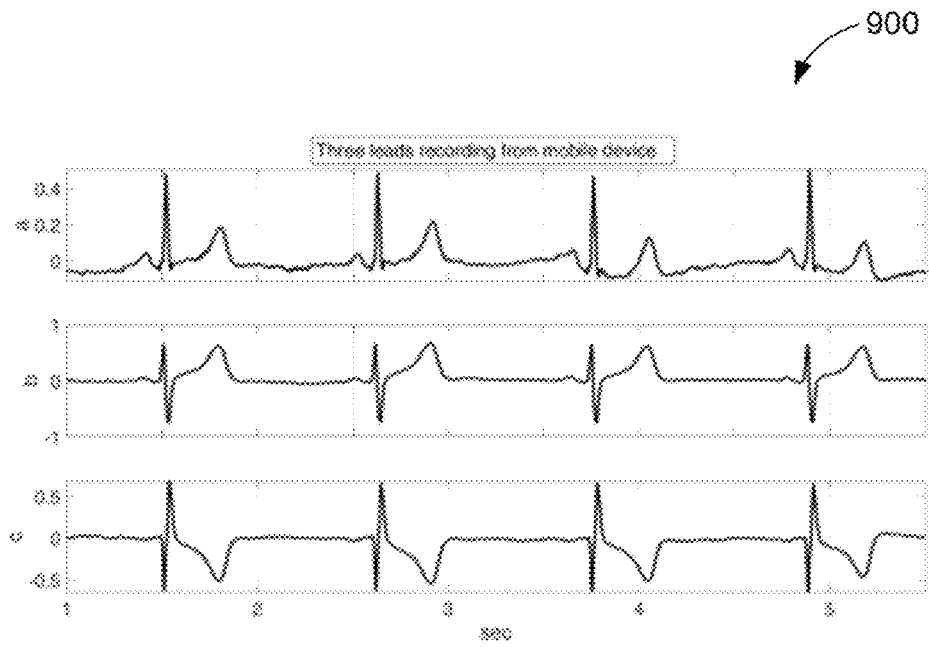
FIG. 9 is a graph of an example 3-lead ECG data, in accordance with some embodiments.

FIG. 9 is a graph of an example 3-lead ECG data 900, in accordance with some embodiments. In some variations, the 3-lead ECG data 900 may also be captured at the first collection time with respect to the 12-lead ECG data 800. For example, the 3-lead ECG data 900 may represent ECG data captured by a portable ECG device 110 by a patient for analysis by a clinician. The 3-lead ECG data 900 may include three leads, such as $X_1$, $X_2$, and $X_3$, as described herein. The leads $X_1$, $X_2$, and $X_3$ may be labeled a, b, and c in FIG. 9.

Figure 10:
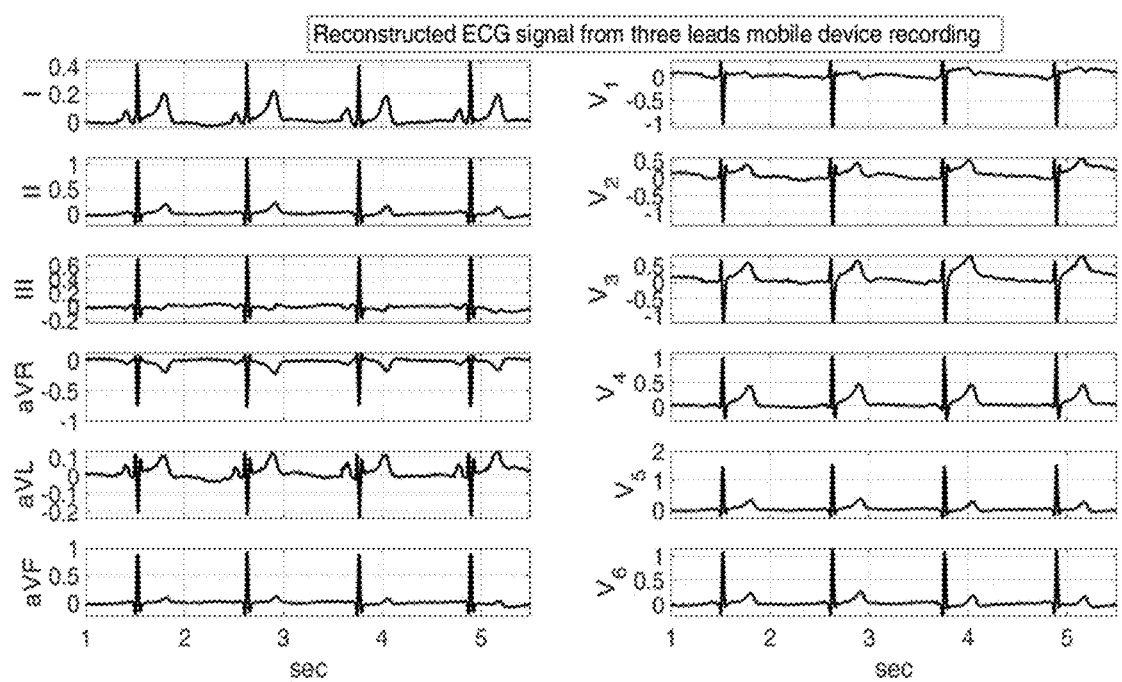
FIG. 10 is a graph of an example synthesized 12-lead ECG data, in accordance with some embodiments.

FIG. 10 is a graph of an example synthesized 12-lead ECG data 1000, in accordance with some embodiments. For example, the synthesized 12-lead ECG data 1000 may be based on the 3-lead ECG data 900 of FIG. 9. In some variations, a set of transformation parameters based on earlier recorded 12-lead ECG data (not shown) may be used to synthesize the 12-lead ECG data 1000. A visual comparison of the 12-lead ECG data 800 and the synthesized 12-lead ECG data 1000 may show that the synthesized 12-lead ECG data 1000 may be relatively similar to the 12-lead ECG data 800. Table 1, below, shows mean differences and associated standard deviations between the 12-lead ECG data 800 and the synthesized 12-lead ECG data 1000. The relatively large mean numbers (e.g., numbers approaching 1.0) indicate a large similarity between the 12-lead ECG data 800 and the synthesized 12-lead ECG data 1000.

TABLE 1

| Lead | Mean | Standard Deviation |
|---|---|---|
| I | 0.94253 | 0.062133 |
| II | 0.940323 | 0.040819 |
| III | 0.840267 | 0.151103 |
| aVR | 0.949895 | 0.04622 |
| aVL | 0.888894 | 0.09409 |
| aVF | 0.867555 | 0.239492 |
| V1 | 0.924239 | 0.080143 |
| V2 | 0.924775 | 0.087036 |
| V3 | 0.901153 | 0.219118 |
| V4 | 0.891144 | 0.252271 |
| V5 | 0.951643 | 0.046939 |
| V6 | 0.953678 | 0.043724 |
| Average | 0.914675 | 0.051309 |

Figure 11:
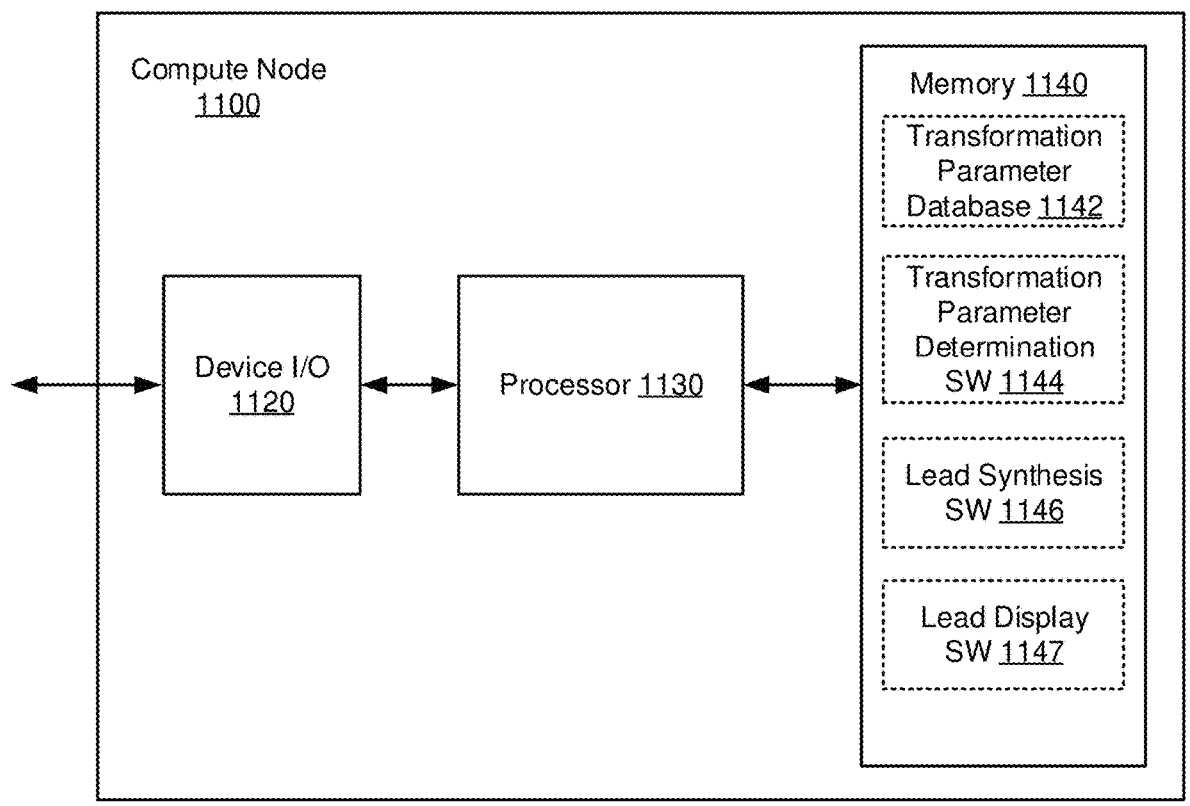
FIG. 11 shows a block diagram of a compute node, in accordance with some embodiments.

FIG. 11 shows a block diagram of a compute node 1100, in accordance with some embodiments. The compute node 1100 may include a device input/output (I/O) interface 1120, a processor 1130, and a memory 1140. The device I/O interface 1120, which may be coupled to a network (not shown), may transmit signals to and receive signals from other wired or wireless devices. For example, the device I/O interface 1120 may transmit and receive data to/from a portable device, such as the ECG device 110 of FIG. 1 or any feasible display for the display of ECG data. In some embodiments, the device I/O interface 1120 may transmit data to handheld devices such as a smart phone, computing tables, laptops, or any other feasible device. Although not shown for simplicity, a transceiver controller may be implemented within the processor 1130 and/or the memory 1140 to control transmit and receive operations of the device I/O interface 1120 including, for example, receiving 3-lead and 12-lead ECG data and transmitting synthesized 12-lead ECG data and associated images.

The processor 1130, which is also coupled to the device I/O interface 1120 and the memory 1140, may be any one or more suitable processors capable of executing scripts or instructions of one or more software programs stored within the compute node 1100 (such as within memory 1140).

The memory 1140 may include a transformation parameter database 1142. The transformation parameter database 1142 may include one or more transformation parameters for one or more patients. In some embodiments, the one or more transformation parameters may include linear transformation matrices that may be used to synthesize 12-lead ECG data from 3-lead ECG data as described, for example, with respect to FIGS. 4 and 7. For example, the compute node 1100 may receive 3-lead ECG data through the device I/O interface 1120 and synthesize (generate) 12-lead ECG data based on the 3-lead ECG data and one or more transformation parameters stored in the transformation parameter database 1142. The synthesized 12-lead ECG data may then be transmitted to any other feasible device through the device I/O interface 1120.

The memory 1140 may also include a non-transitory computer-readable storage medium (e.g., one or more non-volatile memory elements, such as EPROM, EEPROM, Flash memory, a hard-drive, etc.) that may store the following software modules:
a transformation parameter determination software (SW) module 1144 to generate transformation parameters;
a lead synthesis SW module 1146 to synthesize ECG leads; and a lead display SW module 1147 to generate ECG lead data that may be displayed.

Each software module includes program instructions that, when executed by the processor 1130, may cause the compute node 1100 to perform the corresponding function(s). Thus, the non-transitory computer-readable storage medium of the memory 1140 may include instructions for performing all or a portion of the operations listed herein.

The processor 1130 may execute the transformation parameter determination SW module 1144 to determine transformation parameters, including linear transformation matrices to generate (synthesize) 12-lead ECG data from 3-lead ECG data. In some variations, the transformation parameter determination SW module 1144 may include instructions to determine transformation matrices as described with respect to FIG. 4. In some embodiments, the determined transformation parameters may be stored in the memory 1140, such as in the transformation parameter database 1142.

The processor 1130 may execute the lead synthesis SW module 1146 to synthesize ECG leads based at least in part on transformation parameters. For example, execution of the lead synthesis SW module 1146 may generate 12-lead ECG data based on received 3-lead ECG data and transformation parameters. The transformation parameters may be determined with the transformation parameter determination SQ module 1144 and/or stored in the transformation parameter database 1142. In some variations, the lead synthesis SW module 1146 may include instructions to synthesize ECG data as described with respect to FIG. 7.

The processor 1130 may execute the lead display SW module 1147 to generate ECG data that may be displayed to a clinician. For example, execution of the lead display SW module 1147 may generate 12-lead ECG data that may be displayed, where the displayed data is based on the ECG data synthesized based on the lead synthesis SW module 1146.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others.

Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of generating electrocardiogram (ECG) data, the method comprising:
    receiving a current 3-lead ECG data recorded from a patient, wherein the current 3-lead ECG data comprises three orthogonal or pseudo-orthogonal leads;
    generating a derived 12-lead ECG dataset from the current 3-lead ECG data by applying a set of linear transformation parameters, wherein the set of linear transformation parameters are determined based at least in part on a prior 12-lead ECG dataset recorded from the patient at a first earlier collection time and a prior 3-lead ECG dataset recorded from the patient at a second earlier collection time that is different from the first earlier collection time, wherein the prior 3-lead ECG dataset is synchronized with the prior 12-lead ECG dataset by determining a representative beat for both the prior 3-lead ECG dataset and the prior 12-lead ECG dataset, wherein the set of linear transformation parameters comprises a set of transformation matrices that synthesize the prior 12-lead ECG dataset from the prior 3-lead ECG dataset, wherein the prior 3-lead ECG dataset is synchronized with the prior 12-lead ECG dataset by further resampling at least one of the prior 12-lead ECG dataset and the prior 3-lead ECG dataset; and
    outputting the derived 12-lead ECG dataset.

2. The method of claim 1, wherein generating the derived 12-lead ECG dataset comprises segmenting each lead of the prior 12-lead ECG dataset and the prior 3-lead ECG dataset, wherein the set of linear transformation parameters comprises a set of transformation matrices that synthesize segments of the prior 12-lead ECG dataset from segments of the prior 3-lead ECG dataset.

3. The method of claim 1, wherein the prior 3-lead ECG dataset is synchronized with the prior 12-lead ECG dataset by further determining a cross-correlation between the prior 3-lead ECG dataset and the prior 12-lead ECG dataset.

4. The method of claim 1, wherein the prior 3-lead ECG dataset is synchronized with the prior 12-lead ECG dataset by further aligning features of a QRS complex of the prior 12-lead ECG dataset with features of a QRS complex of the prior 3-lead ECG dataset.

5. The method of claim 1, wherein the resampling is in a frequency domain.

6. The method of claim 1, wherein the prior 3-lead ECG dataset is synchronized with the prior 12-lead ECG dataset by further determining the representative beat for both the prior 3-lead ECG dataset and the prior 12-lead ECG dataset based on a median beat or an average beat from a plurality of heartbeats.

7. The method of claim 1, wherein the prior 3-lead ECG dataset is synchronized with the prior 12-lead ECG dataset by further determining the representative beat for both the prior 3-lead ECG dataset and the prior 12-lead ECG dataset by selecting a median heartbeat from each of the prior 12-lead ECG dataset and the prior 3-lead ECG dataset.

8. The method of claim 1, wherein outputting the derived 12-lead ECG dataset comprises displaying the derived 12-lead ECG dataset.

9. The method of claim 1, wherein the leads of the prior 3-lead ECG dataset are orthogonal or pseudo-orthogonal.

10. A method of generating electrocardiogram (ECG) data, the method comprising:
    receiving a current 3-lead ECG data recorded from a patient, wherein the current 3-lead ECG data comprises three orthogonal or pseudo-orthogonal leads;
    generating a derived 12-lead ECG dataset from the current 3-lead ECG data by applying a set of linear transformation parameters, wherein the set of linear transformation parameters are determined based at least in part on a prior 12-lead ECG dataset recorded from the patient at a first earlier collection time and a prior 3-lead ECG dataset recorded from the patient using orthogonal or pseudo-orthogonal leads at a second earlier collection time that is different from the first earlier collection time, wherein the prior 3-lead ECG dataset is synchronized with the prior 12-lead ECG dataset by determining a representative beat for both the prior 3-lead ECG dataset and the prior 12-lead ECG dataset, segmenting each lead of the prior 12-lead ECG dataset and the prior 3-lead ECG dataset, wherein the set of linear transformation parameters comprises a set of transformation matrices that synthesize segments of the prior 12-lead ECG dataset from segments of the prior 3-lead ECG dataset, wherein the prior 3-lead ECG dataset is synchronized with the prior 12-lead ECG dataset by further resampling at least one of the prior 12-lead ECG dataset and the prior 3-lead ECG dataset; and outputting the derived 12-lead ECG dataset.

11. An electrocardiogram (ECG) system comprising:
a portable ECG device configured to record a current 3-lead ECG dataset from a patient; and
a non-transitory computer-readable storage medium comprising instructions that, when executed by one or more processors, cause the one or more processors to perform operations comprising:
  access a first 12-lead ECG dataset for the patient associated with a first dataset collection time;
  access a first 3-lead ECG dataset for the patient associated with a second dataset collection time different than the first dataset collection time; and
  determine a set of linear transformation parameters to synthesize 12-lead ECG dataset based at least in part on the first 12-lead ECG dataset and the first 3-lead ECG data, wherein the first 3-lead ECG dataset is synchronized with the first 12-lead ECG dataset by determining a representative beat for both the first 3-lead ECG dataset and the first 12-lead ECG dataset, wherein the set of linear transformation parameters comprises a set of transformation matrices that synthesize the first 12-lead ECG dataset from the first 3-lead ECG dataset;
  receive the current 3-lead ECG dataset from the portable ECG device;
  synthesize a second 12-lead ECG dataset from the current 3-lead ECG dataset based at least in part on the set of linear transformation parameters;
  synchronize the first 3-lead ECG dataset to the first 12-lead ECG dataset, wherein the synchronization includes a resampling of at least one of the first 12-lead ECG dataset and the first 3-lead ECG dataset; and
  output the second 12-lead ECG dataset.

12. The system of claim 11, wherein the synchronization includes a determination of a cross-correlation between the first 3-lead ECG dataset and the first 12-lead ECG dataset.

13. The system of claim 11, wherein the synchronization includes an alignment of features of a QRS complex of the first 12-lead ECG dataset with features of a QRS complex of the first 3-lead ECG dataset.

14. The system of claim 11, wherein the resampling is in a frequency domain.

15. The system of claim 11, wherein the synchronization includes a determination of representative beats for the first 12-lead ECG dataset and the first 3-lead ECG dataset.

16. The system of claim 15, wherein the determination of representative beats includes a determination of an average or median value of each of the first 12-lead ECG dataset and the first 3-lead ECG dataset based on a plurality of heartbeats.

17. The system of claim 15, wherein the determination of representative beats includes a selection of a median heartbeat from each of the first 12-lead ECG dataset and the first 3-lead ECG dataset.

18. The system of claim 11, wherein the non-transitory computer-readable storage medium is further configured to:
  segment each lead of the first 12-lead ECG dataset and the first 3-lead ECG dataset; and
  determine a set of transformation matrices to synthesize segments of the first 12-lead ECG dataset from segments of the first 3-lead ECG dataset.

19. The system of claim 11, wherein the non-transitory computer-readable storage medium is further configured to generate display dataset based on the second 12-lead ECG dataset.

20. The system of claim 11, wherein leads of the first 3-lead ECG dataset are orthogonal or pseudo-orthogonal.

21. A non-transitory computer-readable storage medium comprising instructions that, when executed by one or more processors of one or more processors, cause the one or more processors to perform operations comprising:
  receiving a first 12-lead ECG dataset for a patient associated with a first dataset collection time;
  receiving a first 3-lead ECG dataset for the patient associated with a second dataset collection time different than the first dataset collection time;
  determine a set of linear transformation parameters based at least in part on the first 12-lead ECG dataset and the first 3-lead ECG data, wherein the first 3-lead ECG dataset is synchronized with the first 12-lead ECG dataset by determining a representative beat for both the first 3-lead ECG dataset and the first 12-lead ECG dataset, wherein the set of linear transformation parameters comprises a set of transformation matrices that synthesize the first 12-lead ECG dataset from the first 3-lead ECG dataset;
  receive a second 3-lead ECG dataset corresponding to the patient;
  synthesize a second 12-lead ECG dataset from the second 3-lead ECG dataset based at least in part on the set of linear transformation parameters;
  synchronize the first 3-lead ECG dataset to the first 12-lead ECG dataset, wherein the synchronization includes a resampling of at least one of the first 12-lead ECG dataset and the first 3-lead ECG dataset; and
  output the second 12-lead ECG dataset.

* * * * *